United States Patent [19]

DiMartino et al.

[11] Patent Number: 4,794,256
[45] Date of Patent: Dec. 27, 1988

[54] FAST NEUTRON PROCESS MEASUREMENT SYSTEM

[75] Inventors: John M. DiMartino, Chicago; John G. Crump, Sr., Palatine, both of Ill.

[73] Assignee: Kay-Ray, Inc., Arlington Heights, Ill.

[21] Appl. No.: 824,418

[22] Filed: Jan. 31, 1986

[51] Int. Cl.⁴ .............................................. G01N 23/09
[52] U.S. Cl. .................................... 250/357.1; 250/390
[58] Field of Search ............ 250/390 E, 390 C, 357.1, 250/392, 390 A, 390 R, 390 I

[56] References Cited

U.S. PATENT DOCUMENTS

| | | | |
|---|---|---|---|
| 3,532,883 | 10/1970 | Dresia et al. | 250/370 |
| 4,152,590 | 5/1979 | Smith, Jr. et al. | 250/270 |
| 4,395,633 | 7/1983 | Mathew | 250/357.1 |
| 4,535,246 | 8/1985 | Shani | 250/392 |
| 4,639,349 | 1/1987 | Baratta et al. | 250/357.1 |

FOREIGN PATENT DOCUMENTS

| | | |
|---|---|---|
| 3028963 | 2/1981 | Fed. Rep. of Germany . |
| 158142 | 12/1982 | German Democratic Rep. . |
| 201514A | 7/1983 | German Democratic Rep. . |
| 1063447 | 3/1967 | United Kingdom . |
| 1180450 | 2/1970 | United Kingdom . |
| 1387007 | 3/1975 | United Kingdom . |

OTHER PUBLICATIONS

Richardson, "Improved Images in 14.5 MeV Neutron Radiography", Materials Evaluation, Apr. 1977, pp. 52–58.
Berger, "Some Experiments in Fast Neutron Radiography", Materials Evaluation, Dec. 1969, pp. 245–253.
Kay-Ray, Inc., Arlington Heights, Ill., Model 4800 X Level System, Model 4760 Level System, Model 4160 Level/Interface Measurement System and Model 3660 Density Measurement System, undated.
Lepper, Jr. H. A., and R. B. Rodgers, "Nuclear Methods for Determining the Water Content and Unit Weight of Fresh Concrete," Journal of Materials, (abstract only), vol. 6, No. 4, (Dec. 1971).
Nagpal, M. K. et al., "Characteristics of a Neutron Moisture Gauge with a Solid State Detector," Publication S3225-0002, Pramana, vol. 1, No. 2, (1973).

Primary Examiner—Carolyn E. Fields
Attorney, Agent, or Firm—Kinney & Lange

[57] ABSTRACT

A process measurement system for measuring levels, interfaces and other characteristics related to products positioned between a fast neutron source and a detector that directly measures the transmitted fast neutrons. The system far exceeds the limitations of neutron backscatter, thermal neutron transmission and gamma techniques while avoiding problems associated with them. As shown, a fast neutron source is placed on one side of a vessel that is being monitored, and a detector is placed on the opposite side. Fast neutrons have excellent penetration properties and thus measurements through thick walls and across substantial distances are possible. A direct measurement of the fast neutrons transmitted through the vessel and/or product is made. This arrangement provides an output that is a direct function of the transmitted fast neutrons between the source and detector, and is not dependent upon inferential measurement where errors are encountered.

12 Claims, 2 Drawing Sheets

FAST NEUTRON PROCESS MEASUREMENT SYSTEM

BACKGROUND OF THE INVENTION

1. Field of the Invention

The present invention relates to measurement systems using high (fast) energy neutron sources, and direct measurement of transmitted fast neutrons which have transited through a measurand.

2. Description of the Prior Art

Fast or high energy neutron sources are known, and are used as transmitting sources in measurement systems, such as moisture detectors. Fast neutrons may be converted to thermal or slow neutrons when they travel in certain materials, especially hydrogen containing materials. Detection, of either backscattered or transmitted thermal neutrons is the basis of such measurements. Operating limits for wall and material thicknesses, sensitivity to system geometry, and capture of thermal neutrons by other elements (e.g. chlorine, boron) in the measured material limit the application and accuracy of such thermal neutron measurement systems. Further, the basis for such measurements are inferred from the quantity of transmitted thermal neutrons detected, based on a quantity of available fast neutrons from the source. Fast neutrons are less subject to scattering or capture by other materials and have greater probability of penetration through such materials than do thermal neutrons. Prior systems have not made use of the advantages offered by the direct measurement of the quantity of fast neutrons for process control and measurements. The use of thermal neutron backscatter, thermal neutron transmission and various gamma radiation techniques for process measurements have long been known. For example, the assignee of the present application, Kay-Ray, Inc. of Arlington Heights, Ill. has made level and interface measurement systems using radiation sources and detection, such as their Model 4800X Level System, the Model 4760 Level System, the Model 4160 Level/Interface Measurement System, and the Model 3660 Density Measurement System. These systems use radiation principles, having sources of radiation and detectors, which provide an output that can be sensed by detection circuitry and then used for control, such as use with microprocessors and two or four wire transmitter systems. These systems all provide noncontact measuring, but rely upon gamma or thermal neutron radiation detection which rate susceptible to absorption by thick walled vessels.

The present invention of measuring the quantity of fast neutrons which have transited through the measurand has adaptation and uses in difficult measurement environments, such as relatively large distances, thick vessel walls, material build-ups on the interior of vessel walls, or thick layers of insulation which greatly affect other types of measurement systems. Fast neutrons do not occur naturally as background radiation, thus it is practical to provide and sense low quantities of fast neutrons. Hence radiation safety considerations are enhanced and potential hazards are minimized and its still possible to provide an adequate quantity of fast neutrons for desired measurement results.

In the prior art, British Patent No. 1,387,007 discloses a fast neutron source made of AmBe(Americum-241) Beryllium, but utilizes thermal neutron detection techniques to circumvent the layer thickness or product profile variations that would be encountered if backscatter measurement techniques were used. Density correction is also incorporated into the measurement by use of gamma absorption in this device. The patent also discloses the use of hydrogen reflectors to increase detector output. This system teaches the transmission of high energy neutrons through a conveyor belt and sample material, and as moisture varies in the product the quanitity of high energy neutrons converted to thermal neutrons varies, and the resulting thermal neutron flux variations are measured and related to moisture content. This configuration limits the amount of material that can be measured since when the material thickness is increased beyond certain limits, beyond such limit, the mean travel distance of the thermal neutrons through the material is exceeded. Hence, the thermal neutron flux is then no longer representative of the measurand.

British Patent No. 1,180,450 shows neutron backscatter techniques for measuring moisture, and deals with increasing the capability of making such measurements accurately through the use of hydrogen reflectors.

Other art shows various detection techniques used for neutron radiation, for example U.S. Pat. No. 3,532,883 teaches moisture detection of solids using neutron radiation and measurement of thermal neutrons transmitted through the material.

An article by Lepper, et al entitled "Nuclear Methods for Determining the Water Content and Unit Weight of Fresh Concrete", J. Materials—Volume 6, No. 4 (Dec. 1971), teaches a method of determining moisture level in solid and concrete material using a fast neutron source and thermal neutron counting device.

DEAK publications DL0158142 and DL0201514 teach methods of measuring moisture in concrete walls by neutron emission. Publication S3225-0002, teaches a method to determine moisture in a deep bore hole by means of using a fast neutron source. However, none of these references teach the measurement of transmission of high energy or "fast" neutrons from a source on one side of a vessel, and directly receiving the fast neutrons or high energy flux on the other side of the vessel and measuring this high energy flux variation directly.

German Patent Application No. 3,028,963 shows a source which emits both fast neutrons and gamma rays through a product, with detectors on the opposite side. The arrangement is used for calculating moisture content of a product on the basis of both the neutron and gamma ray counts. The application does state that neutrons and gamma rays may emanate from separate radiation surces, but both types of radiation are necessary to carry out the intent of the invention. Thus, the detectors used have to be able to sense both neutrons and gamma rays for obtaining or providing the desired output. In the present device, care is taken to insure that the detector is responsive only to the received fast neutrons, which are then converted to thermal neutrons for sensing. The German patent application makes it clear that the gamma rays are required in order to overcome the influence of bulk density of the material in the moisture measurement system disclosed therein.

SUMMARY OF THE INVENTION

The invention relates to a measurement system using high energy or fast neutrons for sensing a parameter or measurand of a material in a chamber and for providing an output indicative of the parameter. A source of fast neutrons disposed on the chamber directs a first flux of fast neutrons in a first direction across the chamber. There is substantially no natural background radiation of fast neutrons and a small source provides a flux of fast neutrons.

A known amount of reduction of fast neutron flux occurs passing through the chamber walls, and detectable reductions occur when the fast neutrons are absorbed or scattered as they pass through the material in the chamber. A detector system is disposed across the chamber from the source for detecting the reduced quantity of fast neutrons. The detector system detects the reduced quantity of fast neutrons but excludes detection of substantially all radiation except fast neutrons travelling in the first direction. The detector system is made large enough in area to sense a sufficient flux of fast neutrons for detection and provide a useable detector output signal. The detector system comprises a fast neutron detector and shielding means. The shielding means is disposed about the detector for shielding the detector from slow neutrons while permitting fast neutrons to enter the detector. The detector provides an output signal representative of fast neutron flux to a sensing means. The output signal is also representative of a parameter of the material in the chamber such as level within a narrow band, interface with a second material, or composition. The detection system is adjusted to calibrate the measurement system for use with the source and the material property to be sensed in the chamber. The measurement system can be installed on an existing chamber to detect level without modifying the chamber,thereby effecting the measurement at substantial savings compared to other measurement systems.

DETAILED DESCRIPTION OF THE PREFERRED EMBODIMENT

Figure 1:
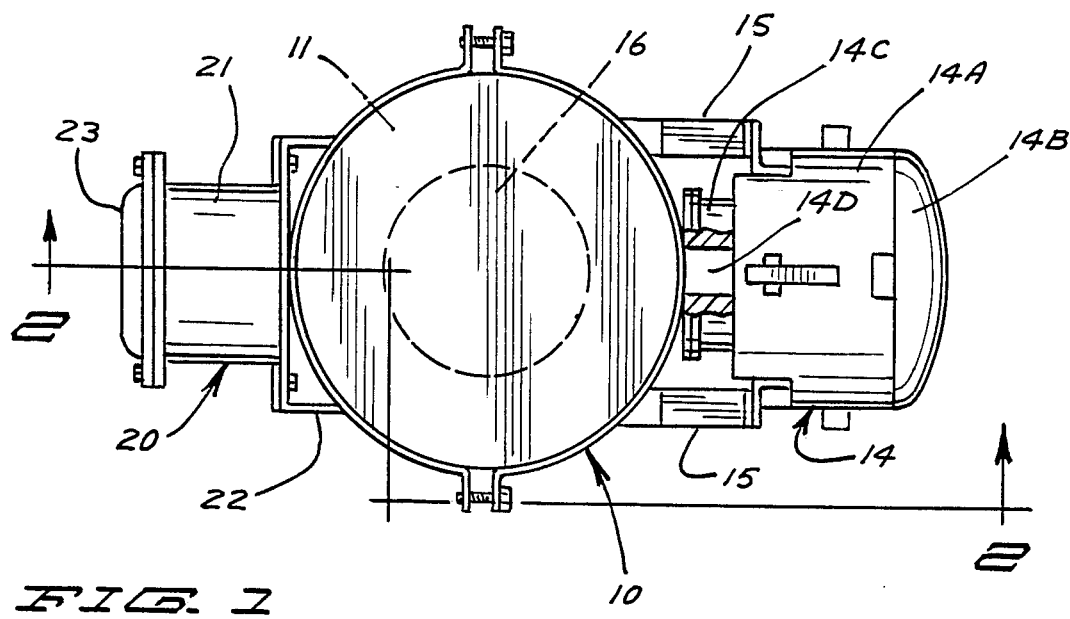
FIG. 1 is a top plan view of a typical vessel in cross section showing a fast neutron source housing and neutron detector system mounted on the vessel for measuring characteristics of a material filling the vessel.
Figure 2:
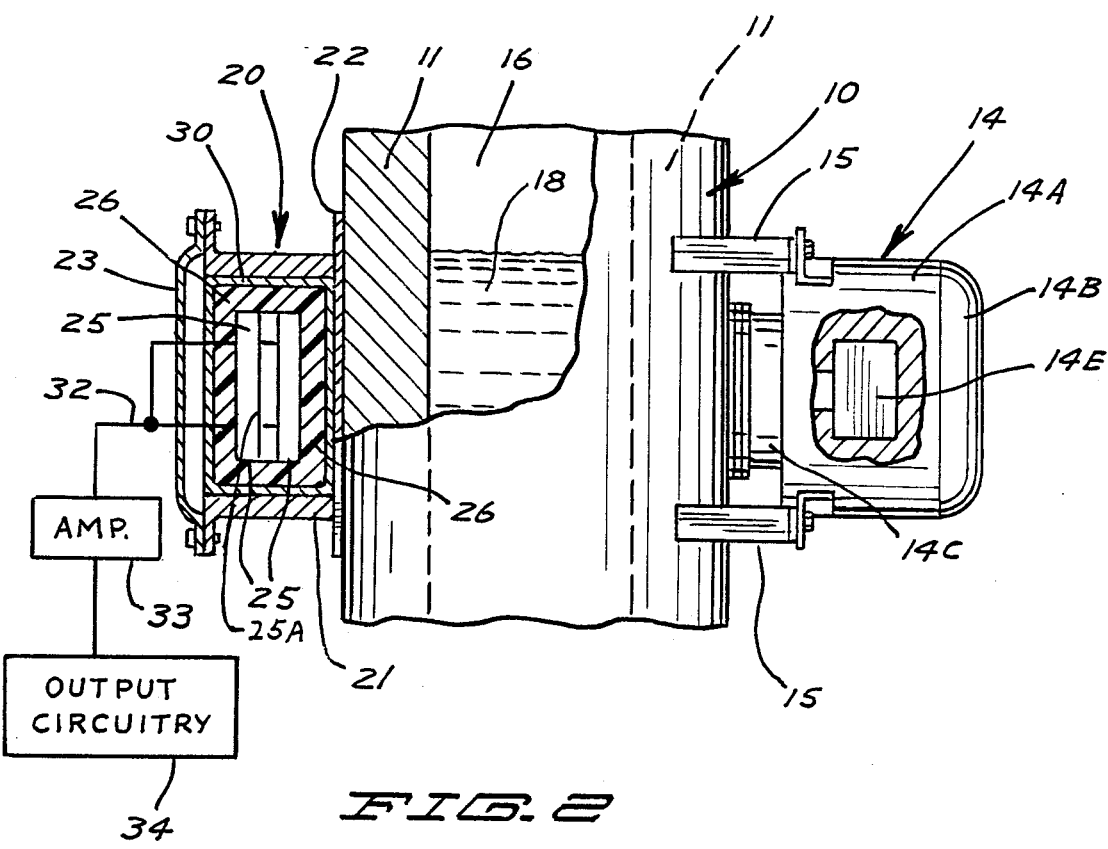
FIG. 2 is a vertical sectional view taken on line 2—2 in FIG. 1 showing schematically the detector system array.

As shown in FIGS. 1 and 2, in a typical installation, a thick wall vessel indicated generally at 10 has the walls 11, made of steel. On one side of the vessel there is a fast neutron source indicated generally at 14 and supported on suitable brackets 15 relative to the vessel. The shell 14A for the fast neutron source provides protection from direct contact with source 14E. Any shielding may have a suitable neutron transparent "window" 14D in a neck 14C, to direct the fast or high energy neutrons across vessel 10.

In the embodiment shown, a 500 milli-Curie (mCi) AmBe source 14E is normally used or other sources such as $Cf^{252}$, $Pu^{244}Be$ may also be employed and this source may be selected in laboratory tests in relation to the vessel and the parameter to be sensed as shown. Source 14E is disposed in the outer shell 14A such that neutrons pass through the window 14D in neck 14C and are directed outwardly therefrom.

The fast neutron source directs neutrons diametrically across the vessel 10, and across the interior space or chamber indicated at 16 which contains a measurand material 18. In the form shown, the level of material 18 is to be detected. The fast neutrons are transmitted through wall 11 on one side of vessel 10, through material 18, and then through the wall 11 on the other side of vessel 10 to a fast neutron detector system indicated generally at 20 that is in an outer housing 21 supported on suitable brackets 22 with respect to the vessel 10. An access cover 23 is suitably held in place on the housing 21.

The high energy or fast neutron detection system 20 enclosed within the explosion proof housing or enclosure 21 is shown in cross section in FIG. 2, and shows a plurality of individual ion chamber detectors 25 (three or more are generally used), which, as shown, are boron trifloride Ion chambers. Boron trifluoride or $He^3$ proportional counters, or thermal neutron sensitive scintillation counters also can be used. Outer housing 21 has an internal lining of relatively thick panels of thermalizing material such hydrogen, or carbon as in polyethylene, indicated at 26. The panels 26 surround the detectors 25 and the fast or high energy neutrons transmitted through the vessel and will pass through the steel outer housing 21 and as they pass through the panels 26 will be changed to thermal neutrons. The change to thermal neutrons occurs after entering the detector package. The neutrons received are thus detected as thermal neutrons by detectors 25. An outer shield or layer of cadmium (or other neutron shielding material) indicated at 30 may be placed around the panels 26, and just inside (lining) the walls of housing 21 to encapsulate the panels 26 and detectors 25. The cadmium or other shield layer 30 blocks external thermal neutrons to thereby insure that only transmitted fast neutrons from source 14 are transmitted to the panels 26 and detectors 25.

The very thick vessel walls, the large distances between the detection system and the source shown, and other configuration factors will provide a means of precluding the detectors 25 from receiving unwanted thermal neutrons which are converted from transmitted fast neutrons from the source 14 before they reach the panels 26. As shown, the cadmium shield layer 30 further obviates transmission of thermal neutrons into the interior of the detector system.

Detectors 25, such as boron trifluoride ionizing chambers, generate small electrical D.C. currents when activated by the received fast neutrons which by then have been converted by panels 26 to thermal neutrons. The signal level is a function of neutron flux levels, and such currents from the individual detectors 25, are summed and provided along an output line indicated at 32 to a D.C. amplifier 33 of conventional design. The circuitry for receiving the signals from detectors 25 is also used in gamma ray detector circuitries previously described and sold by Kay-Ray, Inc., such as in the Kay-Ray ® Model 4700F Level Measurement System. Amplifier 33 amplifies the signal and provides an output to output circuitry indicated at 34 of suitable design to indicate the magnitude of fast neutron transmission through the vessel walls and the measurand material 18 in the interior chamber 16 of the vessel which may intercept or scatter the transmitted neutrons.

The transmitted fast neutrons are at low flux density, and thus, to obtain an adequate output, the area of the active detection system facing the source 14 is selected so as to be large enough to provide usable signals. There is a substantial area of detectors 25 for receiving neutrons from source 14.

The present invention is particularly suitable for sensing hydrogenous material, but the presence of other materials in vessel 10 having a suitable mass can be detected as well. Non-hydrogenous material will scatter a portion of the fast neutrons and thus the presence of such material can also be detected because the number of fast neutrons reaching the detection system 20 will change even when a non-hydrogenous material in the vessel is between the source and detection system.

The basic system has been found experimentally to work well with a 500 mCi AmBe source, which will provide an output of 9 pico amperes at one meter through air when radiated with that source. The fast neutrons from source 14 have high penetrating proportional to the detector output is directly proportional to the transited fast neutron field generated by the fast neutrons which have transited through measurand material 18. When a material to be measured is located between the source and detector, the detector output is easily related to the product level, its composition, or to interfaces between two products. The output may be used for on/off switching applications or for indicating a narrow band, continuous level, as desired.

In the present application, the vessel shown has walls approximately 6 inches thick, as shown. The term "thick wall" is meant to be a steel wall two and one-hald inches or more thick or a wall of refactory brick or concrete having equivalent fast neutron absorbtion properties. However, for use with larger vessels than that shown herein, the following examples can be considered:

A system for monitoring a 10 inch thick steel wall vessel, 3 meters in diameter in an empty condition, a foam filled condition, and a liquid filled condition are provided as examples. The output is proportional to the inverse of the square of the distance.

(1) Detector output at 3 m:

$$\frac{9 \, pA}{d^2} = \frac{9}{d^2} = \frac{9}{3^2} =$$

1 pA in air.

(2) Absorption due to vessel walls:
10"×2=20 inches total steel thickness
The half value is: $\frac{1}{2}$(v) steel=10"
20"/10"=2 one half values or a radiation intensity reduction of 4
The detector current for an empty vessel is thus $\frac{1}{4}$ that of air or a current of 0.25 pA.
This output reduction is due to the steel walls.

(3) Absorption due to foam:
Assume by experimental data an absorption by foam of three half values or a reduction factor of 8.
Detector current-with vessel filled with foam 0.25/8=0.03 pA (4) Absorption due to a liquid:
Assume the liquid fully absorbs the remaining neutron radiation
Detector current vessel filled with liquid is thus less than 0.01 pA.

From the above analysis, it can be seen that by setting the range of input currents of 0 to 0.25 pA, the amplified output can be calibrated to indicate an empty vessel, a foam filled vessel, and a liquid filled vessel. This output current level is well within the measurement capabilities of existing amplifiers and associated electronics. The sensing area of the detectors is positioned to provide maximum sensed neutron flux levels.

By having the detector shielded to prevent receiving anything except the high energy neutrons (by geometry, space, or a thermal neutron shielding layer), a direct measurement of the transmission of high energy neutrons is obtained, and indications of product level, the presence of a foam on top of a liquid, or merely air in the chamber can be indicated.

The device provides a very accurate detection system, which is not susceptible to the normal problems involved with gamma ray measurements, and far exceeds the capabilities of any system making direct measurements of the thermal neutron flux.

The example cited above would not be possible by non-contacting, non-intrusive measurement of the thermal neutron flux since the thermal neutrons would be incapable of penetrating the 10" steel walls to be measured. Gamma radiation could be used to make the measurement but a Cs 137 radioactive source at least five hundred thousand times larger would be required.

The detectors 25 are preferably ionization chamber type detectors. They each comprise a concentric anode and cathode mounted in a chamber filled with boron trifluoride. The chamber is defined within a steel casing 25A as shown in the drawings. When thermal neutrons penetrate casing 25A, alpha particles are released from the boron causing ionization of the gas and causing an electrical current flow between the anode and cathode in proportion to the neutrons which penetrate the casing. The anode and cathode are connected to the sensing circuitry which measures the current flows. These detectors are known and reliable, and provide appropriate output for use with the present system.

The location and number of the detectors 25 can be changed to suit desired applications. As shown in FIG. 2, simple level and interface signals can be provided. As the level within the vessel changes, the output of the detectors will also change in proportion to the level of product, which converts part of the neutrons transmitted to thermal neutrons. Utilizing a suitable summing circuit it can be determined when the material has reached a preselected level.

Interface detection between two different products is carried out using the same arrangement, in that the number of fast neutrons transmitted by different products having different characteristics is different. Thus, one material between the source and detector provides a known signal, and when the interface with the second material is reached the output of the detectors 25 will change. The arrival of the interface can be determined as to position by proper calibration. The output levels of the detector can be compared to a reference signal and a suitable summing circuit set so that at a null position, or at any other desired value, it is known that the interface is adjacent a selected level.

Conversely, the detectors 25 and source 14 can be mounted to be moved along a vessel, and the position encoded with respect to a reference plane, such as one end of the vessel. When the output of the circuit is at a null or some desired calibration level it will indicate that the interface between two products has been detected and is at the location reached by the source and detector.

In level sensing applications, that is, applications where the level of a product in a vessel is being monitored. The detector system would include detectors that are elongated along the longitudinal axis of the vessel, or in the direction in which level is to be sensed. For example, more than one detector can be placed along the measurement axis and provide a single output signal. The output is proportional to the level of the material, in that the higher the level of material, the less fast neutrons that are transmitted across the vessel causing a lower output signal from the detectors. The output can be used to drive a level indicator that provides an indication of the level.

If a narrow band of material level is to be determined, a detector such as that shown in FIG. 2 may be used, and the output is proportional to the length of the detectors 25 that is covered by product between the source and detector.

The particular application for determining product interface, continuous level, high and low levels are presently carried out with gamma ray detectors as shown in a product brochure of Kay-Ray Inc., the assignee of this application, for their Model 4760 Level Measurement System.

Figure 3:
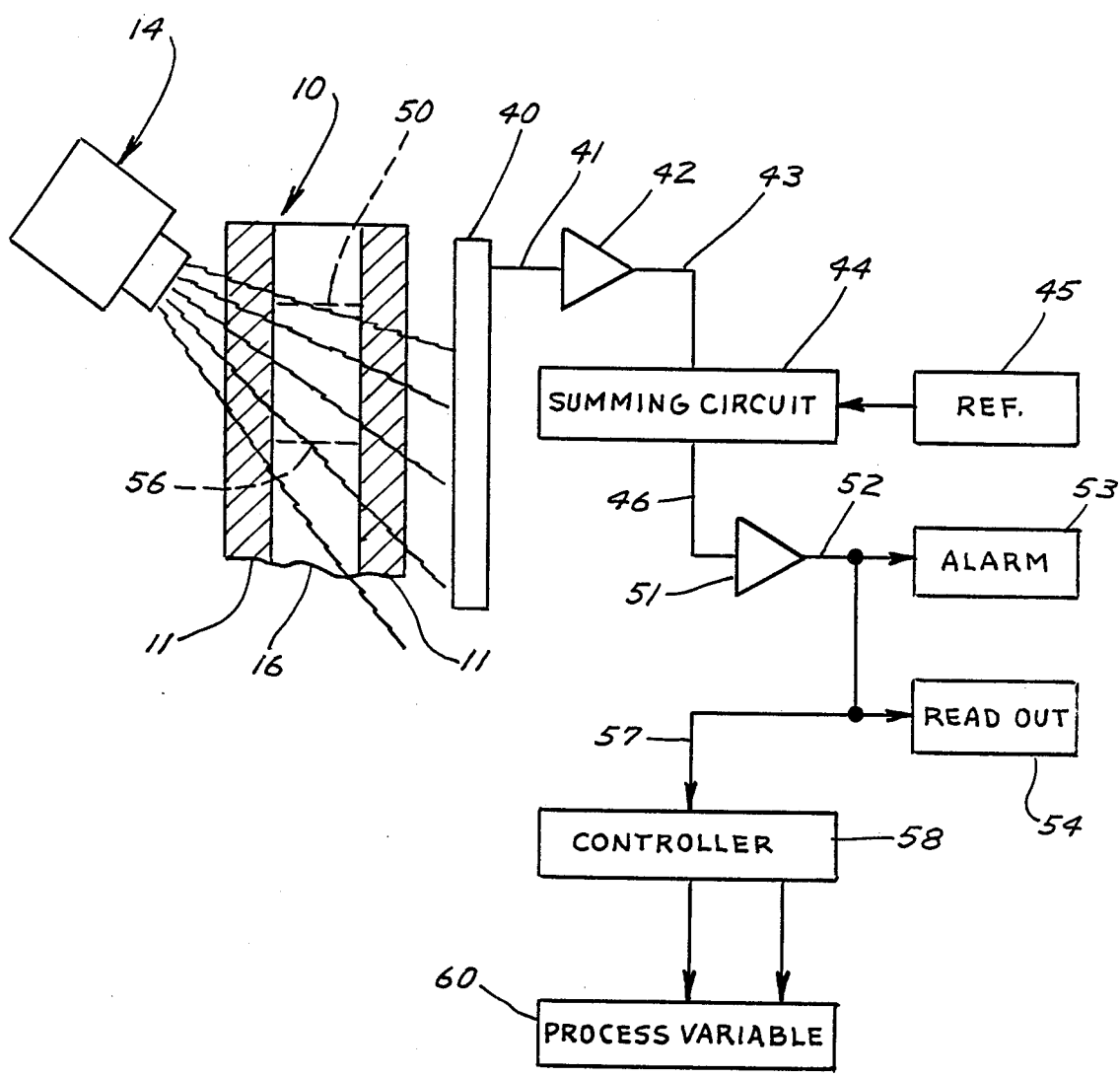
FIG. 3 is a schematic block diagram of the elements of the present invention.

Referring to FIG. 3, a schematic diagram illustrating operation of the present invention is shown. The radiation source 14 is shown on one side of a thick walled vessel 10 having wall 11 defining an interior chamber 16 in which product is placed.

The detector system 40 is shown as being elongated along the longitudinal axis of the vessel, and is shown only schematically. It is the same type of detector system as previously explained, or may be another suitable radiation detector that will provide an output along a line 41 proportional to the fast neutrons that have transited vessel 10. The path of transmitted fast neutrons is represented by lines from the source to the detector system 40.

The output line 41 is connected to a suitable amplifier 42, and provides an amplified output on line 43 that is proportional to the fast neutrons that are received by the detector system 40. The fast neutrons are sensed as previously explained. In this form of the invention the output on line 43 is fed to a summing circuit 44 that has an adjustable reference input 45, so that an output from the summing circuit along a line 46 will be scaled to a set reference point. If, for example, a particular level of product (as indicated by the dotted line 50) is to be detected, the output on line 46 could be nulled at that time, providing a signal through an amplifier 51 along a line 52 to an alarm circuit 53 or directly to a readout system 54.

The output signal will vary as a function of the neutron flux being received by the detector system 40, and thus if the level of material is lower than line 50, such as that indicated by dotted line 56, the output signal along line 41 will be increased because more fast neutrons will be received by the detector system, and this will provide a signal on line 46 that is representative of the neutron flux. The signal is amplified by amplifier 51 and can be provided to read out system 54 which can be calibrated to indicate the material level. The signal also can be provided along an output line 57, to a controller, such as a conventional two wire controller indicated at 58 which is used to control process variables indicated by block 60 so that the product level can be restored to a desired level, controlled at a desired level, or when the material has reached or is held at a particular level, additional operations in the process can be accomplished.

Low product or material level can also be detected by having a separate fast neutron source and detector system at the lower end of the vessel, and if desired detectors can be placed at both the upper end and lower end of a vessel to determine when high range and low range levels have been reached.

The present system can, if desired, also be used for determining moisture of a product, although the most important advantages are achieved when the present invention is used in connection with thick walled vessels for determing single point or continuous levels. Another example of a typical use is determining ammonia levels within an ammonia reactor vessel. Another typical application is for determining material levels in a sulfite digester used in paper making processes. These applications involve thick walled vessels containing the product, and the levels can be quickly and easily determined, without modifying the vessel walls.

The fast neutron source 14 and detection system 20 are easily mounted on existing thick walled pressure vessels, conduits, vertical stacks or the like without the need to modify the thick walls or otherwise change the vessel or stack. The fast neutron source is placed in a desired location on one side of such vessel or stack in any desired manner and the detection system 20 is placed on the opposite side. The fast neutron will be transmitted through existing thick walls, of steel, refactory brick or concrete (or composite walls made of steel lined with another dense material such as refactory brick) and the detection system will change in output when material within such vessel or stack is present at a location between the source and detection system.

Although the present invention has been described with reference to preferred embodiments, workers skilled in the art will recongize that changes may be made in form and detail without departing from the spirit and scope of the invention.

What is claimed is:

1. A fast neutron detection system for monitoring conditions in a chamber of a thick walled vessel having vessel walls of fast neutron absorption characteristics equal to or greater than a steel wall approximately two and one-half inches thick, comprising;
    a fast neutron source directing fast neutrons in a first direction from the exterior of the vessel through one thick wall portion and across the chamber;
    a detector system mounted across the chamber being monitored for determining the transmission of fast neutrons from the source across the chamber, said detector system being disposed on the exterior of a second thick wall portion of the vessel to provide an output representative of high energy neutron transmission from the fast neutron source across the chamber through two wall thicknesses; and
    means for sensing the output from the detector system.

2. The system as specified in claim 1 wherein said detector system comprises a thermal neutron detector, a first layer of material
    surrounding said thermal neutron detector to convert fast neutrons to thermal neutrons, and a second layer of neutron shielding material around said first layer, said second layer transmiting substantially only fast neutrons from the source to the first layer and thus to the thermal neutron detector.

3. The system of claim 2 wherein said first layer comprises a plastic material.

4. The system as specified in claim 1 wherein said fast neutron source comprises Americium 241 Beryllium.

5. The system as specified in claim 1 wherein the sensing means includes means for indicating a level of material in the chamber.

6. The system as specified in claim 1 wherein the sensing means includes means for detecting the presence of an interface in the chamber.

7. In combination with a thick walled vessel having vessel walls of fast neutron absorption characteristics equal to or greater than a steel wall approximately two and one-half inches thick and defining an interior chamber, the chamber containing a material a condition of which is to be sensed, the improvement comprising:
- a high energy neutron source directing high energy neutrons in a first through direction across the chamber through one thick wall of such vessel;
- a detector system mounted on an opposite side of such vessel on the exterior of a second thick wall for determining the intensity of high energy neutrons from the source transmitted across the chamber, so as to give a direct indication of high energy neutron transmission through the thick walls and chamber; and
- means for sensing the output from the detector system.

8. The improvement as specified in claim 7 wherein said detector system comprises a thermal neutron detector, and a first layer of material containing thermalizing material surrounding said thermal neutron detector to convert high energy neutrons to thermal neutrons.

9. The improvement of claim 8 and a second layer of neutron shielding material around said first layer, said second layer transmitting substantially only high energy neutrons from the source to the first layer and thus to the thermal neutron detector.

10. The improvement of claim 8 wherein said first layer comprises a plastic material.

11. A method of determining characteristics of a product located in a space encompassed by thick walls, each wall having fast neutron absorption characteristics equal to or greater than a steel wall approximately two and one-half inches thick, comprising the steps of:
- providing a source of high energy neutrons on one side of the space on the exterior of one thick wall portion, and transmitting the high energy neutrons across the space;
- providing a detector system for detecting substantially only high energy neutrons on the opposite side of said space on the exterior of a second thick wall portion;
- converting the high energy neutrons received by the detector sytem to thermal neutrons for sensing; and
- providing an output signal proportional to the output of the detector system.

12. The method of claim 11 wherein the step of providing a detector system includes the step of locating the detector system to receive high energy neutrons transmitted by the source across the space, and substantially exclude other radiation including thermal neutrons from outside the detector system.

* * * * *

UNITED STATES PATENT AND TRADEMARK OFFICE
CERTIFICATE OF CORRECTION

PATENT NO. : 4,794,256

DATED : December 27, 1988

INVENTOR(S) : John M. DiMartino et al.

It is certified that error appears in the above-identified patent and that said Letters Patent is hereby corrected as shown below:

Col. 1, Line 50, delete "rate" and insert --are--.

Col. 5, Lines 14-15, delete "proportional to" and insert --characteristics and--.

Col. 5, Line 26, delete "hald" and insert --half--.
Col. 8, Line 25, after "walls" delete "of".
Col. 8, Line 41, delete the "semicolon" and insert a colon.
Col. 8, Line 62, delete "transmiting" and insert -- transmitting --.

Signed and Sealed this

Fifteenth Day of August, 1989

Attest:

DONALD J. QUIGG

*Attesting Officer*  *Commissioner of Patents and Trademarks*